US012661043B2

(12) United States Patent
Edelhauser et al.

(10) Patent No.: US 12,661,043 B2
(45) Date of Patent: *Jun. 23, 2026

(54) BIOLOGICAL FLUID COLLECTION AND STABILIZATION SYSTEM

(71) Applicant: Becton, Dickinson and Company, Franklin Lakes, NJ (US)

(72) Inventors: Adam Edelhauser, Kinnelon, NJ (US); Bradley M. Wilkinson, North Haledon, NJ (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 714 days.

This patent is subject to a terminal disclaimer.

(21) Appl. No.: 18/089,133

(22) Filed: Dec. 27, 2022

(65) Prior Publication Data

US 2023/0138146 A1 May 4, 2023

Related U.S. Application Data

(63) Continuation of application No. 16/967,315, filed as application No. PCT/US2019/016520 on Feb. 4, 2019, now Pat. No. 11,540,756.

(60) Provisional application No. 62/626,904, filed on Feb. 6, 2018.

(51) Int. Cl.
*A61B 5/15* (2006.01)
*A61B 5/157* (2006.01)

(52) U.S. Cl.
CPC .. *A61B 5/150755* (2013.01); *A61B 5/150236* (2013.01); *A61B 5/150259* (2013.01); *A61B 5/150351* (2013.01); *A61B 5/150992* (2013.01); *A61B 5/157* (2013.01)

(58) Field of Classification Search
CPC ........ A61B 5/150755; A61B 5/150236; A61B 5/150259; A61B 5/150351; A61B 5/150992; A61B 5/157; A61B 5/153; A61B 5/15003
See application file for complete search history.

(56) References Cited

U.S. PATENT DOCUMENTS

| | | | |
|---|---|---|---|
| 4,653,511 A | 3/1987 | Goch | |
| 5,086,783 A | 2/1992 | Macors et al. | |
| 2005/0054949 A1 | 3/2005 | McKinnon et al. | |
| 2008/0312576 A1 | 12/2008 | McKinnon et al. | |

(Continued)

FOREIGN PATENT DOCUMENTS

| | | |
|---|---|---|
| CA | 2380042 A1 | 9/2002 |
| CN | 204170096 U | 2/2015 |

(Continued)

*Primary Examiner* — Matthew Kremer
*Assistant Examiner* — Nidhi N Patel
(74) *Attorney, Agent, or Firm* — The Webb Law Firm

(57) ABSTRACT

A biological fluid collection system that receives a sample and provides flow-through blood stabilization technology and a precise sample dispensing function for point-of-care and near patient testing applications is disclosed. A biological fluid collection system of the present disclosure is able to effectuate distributed mixing of a sample stabilizer within a blood sample and dispense the stabilized sample in a controlled manner. In this manner, a biological fluid collection system of the present disclosure enables blood micro-sample management, e.g., passive mixing with a sample stabilizer and controlled dispensing, for point-of-care and near patient testing applications.

17 Claims, 11 Drawing Sheets

(56)                    References Cited

U.S. PATENT DOCUMENTS

| | | | |
|---|---|---|---|
| 2014/0261877 | A1 | 9/2014 | Ivosevic et al. |
| 2014/0296744 | A1 | 10/2014 | Wei Li et al. |
| 2014/0305196 | A1 | 10/2014 | Ellis et al. |
| 2014/0308165 | A1 | 10/2014 | Marchiarullo et al. |
| 2014/0309551 | A1 | 10/2014 | Burkholz et al. |
| 2014/0309552 | A1 | 10/2014 | Hoong Sim et al. |
| 2014/0309553 | A1 | 10/2014 | Spatafore et al. |
| 2014/0309556 | A1 | 10/2014 | Fletcher et al. |
| 2016/0103046 | A1 | 4/2016 | Ivosevic et al. |
| 2016/0262679 | A1 | 9/2016 | Ivosevic et al. |
| 2016/0367177 | A1 | 12/2016 | Edelhauser et al. |
| 2017/0059550 | A1 | 3/2017 | Bokka Srinivasa Rao et al. |

FOREIGN PATENT DOCUMENTS

| | | | |
|---|---|---|---|
| DK | 151685 | B | 12/1987 |
| EP | 3018464 | A1 | 5/2016 |
| EP | 2986219 | B1 | 11/2017 |
| RU | 2330616 | C1 | 8/2008 |
| RU | 2509533 | C2 | 3/2014 |
| WO | 2013059431 | A1 | 4/2013 |
| WO | 2014172234 | A1 | 10/2014 |

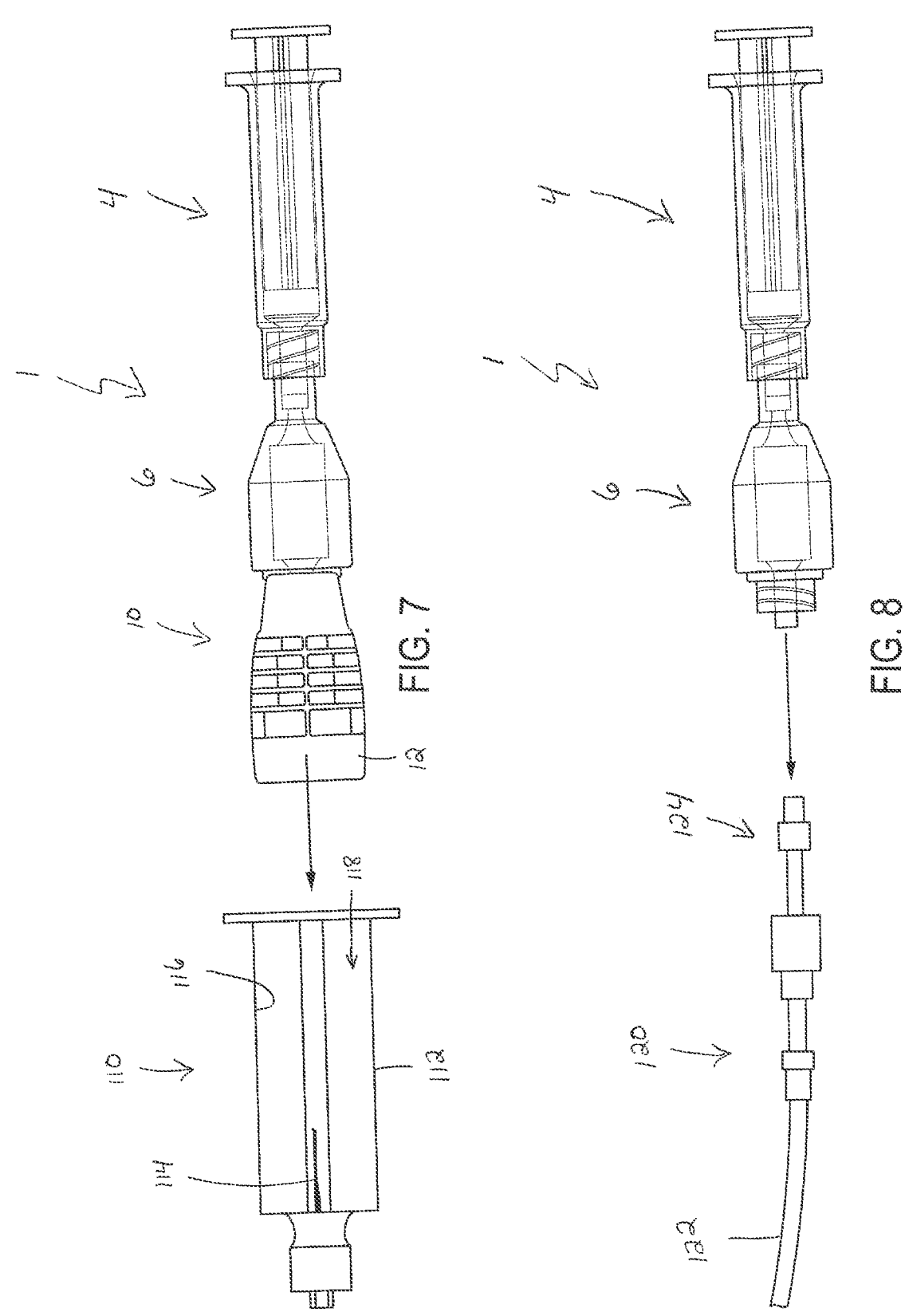

BIOLOGICAL FLUID COLLECTION AND STABILIZATION SYSTEM

CROSS-REFERENCE TO RELATED APPLICATIONS

This application is a continuation of U.S. patent application Ser. No. 16/967,315 entitled "Biological Fluid Collection and Stabilization System" filed Feb. 4, 2019, which is the United States national phase of International Application No. PCT/US2019/016520 filed Feb. 4, 2019, and claims priority to U.S. Provisional Application Ser. No. 62/626,904 entitled "Biological Fluid Collection and Stabilization System" filed Feb. 6, 2018, the disclosures of which are hereby incorporated by reference in their entirety.

BACKGROUND OF THE INVENTION

1. Field of the Disclosure

The present disclosure relates generally to a biological fluid collection system. More particularly, the present disclosure relates to a biological fluid collection device with flow-through blood stabilization and precise sample dispensing of a portion of the sample into a device for analyzing the sample such as a point-of-care or a near-patient-testing device.

2. Description of the Related Art

Blood sampling is a common health care procedure involving the withdrawal of at least a drop of blood from a patient. Blood samples are commonly taken from hospitalized, homecare, and emergency room patients either by finger stick, heel stick, or venipuncture. Once collected, blood samples may be analyzed to obtain medically useful information including, for example, chemical composition, hematology, and coagulation.

Blood tests determine the physiological and biochemical states of the patient, such as disease, mineral content, drug effectiveness, and organ function. Blood tests may be performed in a clinical laboratory or at the point-of-care near the patient.

SUMMARY OF THE INVENTION

The present disclosure provides a biological fluid collection system that receives a sample and provides flow-through blood stabilization technology and a precise sample dispensing function for point-of-care and near patient testing applications. A biological fluid collection system of the present disclosure is able to effectuate distributed mixing of a sample stabilizer within a blood sample and dispense the stabilized sample in a controlled manner. In this manner, a biological fluid collection system of the present disclosure enables blood micro-sample management, e.g., passive mixing with a sample stabilizer and controlled dispensing, for point-of-care and near patient testing applications.

In accordance with an embodiment of the present invention, a biological fluid collection system adapted to receive a sample includes a mixer having a first mixer end and a second mixer end; a sample stabilizer disposed within the mixer; and a syringe assembly having a collection chamber, the syringe assembly removably connectable with the second mixer end, the syringe assembly creates a vacuum that draws the sample through the mixer and into the collection chamber.

In one configuration, the biological fluid collection system includes a closure removably connectable with the first mixer end. In another configuration, the closure includes a cap having a first cap end, a second cap end, and defining a cap channel therein, the cap having a pierceable self-sealing stopper within a portion of the cap channel and a cap connection portion at the second cap end; and an adapter having a first adapter end, a second adapter end, and defining an adapter channel therein, the adapter having an adapter connection portion at the first adapter end, the cap connection portion removably connectable with the adapter connection portion. In yet another configuration, with the cap connected to the adapter, the closure is connectable to a first blood collection device via the cap, and with the cap disconnected from the adapter, the closure is connectable to a second blood collection device via the adapter. In one configuration, the first blood collection device is a tube holder. In another configuration, the second blood collection device is a line ending in a Luer connector. In yet another configuration, the syringe assembly includes a barrel defining a collection chamber and having a first end, a second end, and a sidewall therebetween; a stopper slidably disposed within the collection chamber of the barrel, the stopper sized relative to the collection chamber to provide sealing engagement with the sidewall of the barrel, the stopper transitionable between a first stopper position, in which the stopper is a first distance from the first end of the barrel, and a second stopper position, in which the stopper is a second distance from the first end of the barrel, the second distance greater than the first distance; and a plunger having a first plunger end and a second plunger end, a portion of the first plunger end engaged with the stopper, wherein movement of the plunger away from the first end of the barrel moves the stopper to the second stopper position thereby creating the vacuum that draws the sample through the mixer and into the collection chamber. In one configuration, with the syringe assembly connected to the mixer, the barrel is in fluid communication with the mixer. In another configuration, the mixer effectuates distributed mixing of the sample stabilizer within the sample. In yet another configuration, the mixer includes a material including pores; and a dry anticoagulant powder within the pores of the material. In one configuration, the sample dissolves and mixes with the dry anticoagulant powder while passing through the material. In another configuration, the material is an open cell foam. In yet another configuration, the sample stabilizer is the dry anticoagulant powder. In one configuration, the sample is a blood sample.

In accordance with another embodiment of the present invention, a biological fluid collection and testing system adapted to receive a sample includes a biological fluid collection device comprising a mixer having a first mixer end and a second mixer end; a sample stabilizer disposed within the mixer; a syringe assembly having a collection chamber, the syringe assembly removably connectable with the second mixer end, the syringe assembly creates a vacuum that draws the sample through the mixer and into the collection chamber; and a closure removably connectable with the first mixer end; and a testing device having a receiving port adapted to receive a portion of the syringe assembly for closed transfer of at least a portion of the sample from the syringe assembly to the testing device.

In one configuration, the closure includes a cap having a first cap end, a second cap end, and defining a cap channel therein, the cap having a pierceable self-sealing stopper within a portion of the cap channel and a cap connection portion at the second cap end; and an adapter having a first adapter end, a second adapter end, and defining an adapter channel therein, the adapter having an adapter connection portion at the first adapter end, the cap connection portion removably connectable with the adapter connection portion. In another configuration, with the cap connected to the adapter, the closure is connectable to a first blood collection device via the cap, and with the cap disconnected from the adapter, the closure is connectable to a second blood collection device via the adapter. In yet another configuration, the first blood collection device is a tube holder. In one configuration, the second blood collection device is a line ending in a Luer. In another configuration, the syringe assembly includes a barrel defining a collection chamber and having a first end, a second end, and a sidewall therebetween; a stopper slidably disposed within the collection chamber of the barrel, the stopper sized relative to the collection chamber to provide sealing engagement with the sidewall of the barrel, the stopper transitionable between a first stopper position, in which the stopper is a first distance from the first end of the barrel, and a second stopper position, in which the stopper is a second distance from the first end of the barrel, the second distance greater than the first distance; and a plunger having a first plunger end and a second plunger end, a portion of the first plunger end engaged with the stopper, wherein movement of the plunger away from the first end of the barrel moves the stopper to the second stopper position thereby creating the vacuum that draws the sample through the mixer and into the collection chamber.

BRIEF DESCRIPTION OF THE DRAWINGS

The above-mentioned and other features and advantages of this disclosure, and the manner of attaining them, will become more apparent and the disclosure itself will be better understood by reference to the following descriptions of embodiments of the disclosure taken in conjunction with the accompanying drawings, wherein:

FIG. 7 is a perspective view of a biological fluid collection system being connected to a first blood collection device in accordance with an embodiment of the present invention.

FIG. 8 is a perspective view of a biological fluid collection system being connected to a second blood collection device in accordance with an embodiment of the present invention.

Corresponding reference characters indicate corresponding parts throughout the several views. The exemplifications set out herein illustrate exemplary embodiments of the disclosure, and such exemplifications are not to be construed as limiting the scope of the disclosure in any manner.

DETAILED DESCRIPTION

Figure 1:
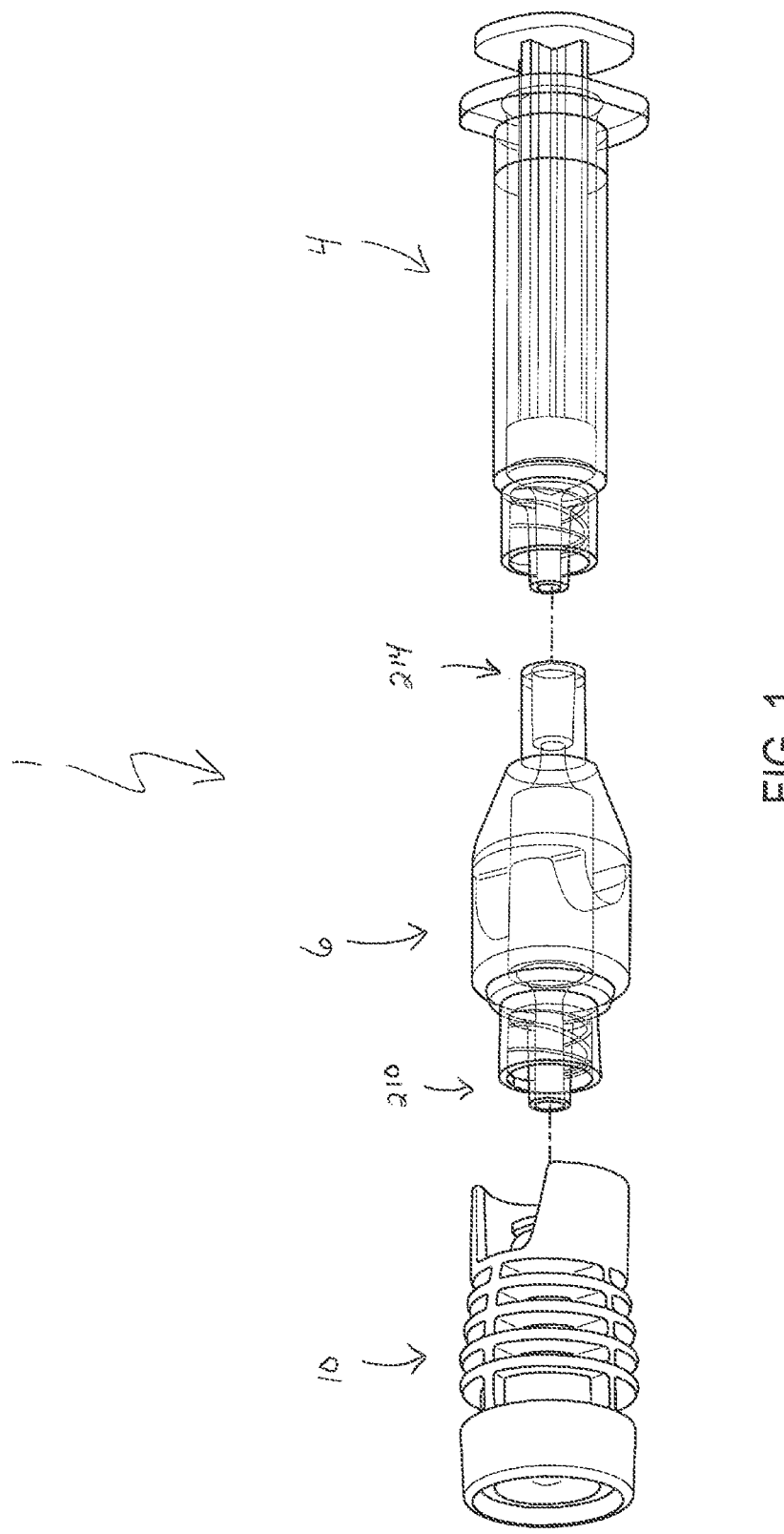
FIG. 1 is an exploded view of a biological fluid collection system in accordance with an embodiment of the present invention.

The following description is provided to enable those skilled in the art to make and use the described embodiments contemplated for carrying out the invention. Various modifications, equivalents, variations, and alternatives, however, will remain readily apparent to those skilled in the art. Any and all such modifications, variations, equivalents, and alternatives are intended to fall within the spirit and scope of the present invention.

For purposes of the description hereinafter, the terms "upper", "lower", "right", "left", "vertical", "horizontal", "top", "bottom", "lateral", "longitudinal", and derivatives thereof shall relate to the invention as it is oriented in the drawing figures. However, it is to be understood that the invention may assume various alternative variations, except where expressly specified to the contrary. It is also to be understood that the specific devices illustrated in the attached drawings, and described in the following specification, are simply exemplary embodiments of the invention. Hence, specific dimensions and other physical characteristics related to the embodiments disclosed herein are not to be considered as limiting.

The present disclosure provides a biological fluid collection system that receives a sample and provides flow-through blood stabilization technology and a precise sample dispensing function for point-of-care and near patient testing applications. A biological fluid collection system of the present disclosure is able to effectuate distributed mixing of a sample stabilizer within a blood sample and dispense the stabilized sample in a controlled manner. In this manner, a biological fluid collection system of the present disclosure enables blood micro-sample management, e.g., passive mixing with a sample stabilizer and controlled dispensing, for point-of-care and near patient testing applications.

Advantageously, a biological fluid collection device of the present disclosure provides a consistent blood sample management tool for point-of-care and near patient testing applications, blood draw, passive mixing technology, and controlled small sample dispensing capability to point-of-care cartridge and standard Luer interfaces with near patient testing receiving ports.

A biological fluid collection system 1 of the present disclosure utilizes a mixer 6 and a closure 10 with a syringe 4. The syringe 4 and closure 10 allow a user to draw a sample 2 from multiple different blood collection devices, such as a Luer line, a tube holder, or other blood collection devices. The syringe 4 also allows for easy drawing of a sample 2 and dispensing of a stabilized sample. The use of a mixer 6 enables automatic mixing of a sample stabilizer 8, such as an anticoagulant, and a blood sample 2 before collection within the syringe 4. The syringe 4 also provides a vacuum to draw in a blood sample 2 and functions as a dispensing mechanism for transfer of a stabilized blood sample 2 to testing devices, cartridges, or benchtop instruments.

Referring to FIGS. 1-6, in one embodiment, a biological fluid collection system 1 of the present disclosure is adapted to receive a biological fluid sample, such as a blood sample 2, and includes a syringe assembly 4, a mixer 6, a sample stabilizer 8, and a closure 10.

The biological fluid collection system 1 of the present disclosure includes a closure 10. FIGS. 1-3 and 7-12 illustrate an exemplary embodiment of a closure 10 of the present disclosure. In one embodiment, a closure 10 of the present disclosure includes a cap 12 and an adapter or connector 14. In another embodiment, the closure 10 may comprise an integral cap and adapter configuration. The closure 10 of the present disclosure allows for connection to multiple different blood collection devices. Referring to FIG. 7, in a first configuration, with the cap 12 connected to the adapter 14, the closure 10 may be connected to a first blood collection device 110 via the cap 12. In some embodiments, the cap 12 can be directly connected to a first blood collection device 110 without the adapter 14. In one embodiment, the first blood collection device 110 includes a tube holder 112. In a second configuration, with the cap 12 disconnected from the adapter 14, the closure 10 may be connected to a second blood collection device 120 via the adapter 14. Referring to FIG. 8, in some embodiments, the closure 10 can be removed and the first mixer end 210 of the mixer 6 can be connected to a second blood collection device 120. In one embodiment, the second blood collection device 120 includes a line 122 ending in a Luer connector 124.

In one embodiment, referring to FIGS. 1-3 and 9-12, the closure 10 includes a cap 12 and an adapter 14. In another embodiment, the closure 10 may comprise an integral cap and adapter configuration. The cap 12 includes a first cap end 20, a second cap end 22, and defines a cap channel 24 therein. The cap 12 has a pierceable self-sealing stopper 26 within a portion of the cap channel 24 and a cap connection portion 28 at the second cap end 22. In one embodiment, the cap connection portion 28 comprises a first Luer connection portion.

Figure 12:
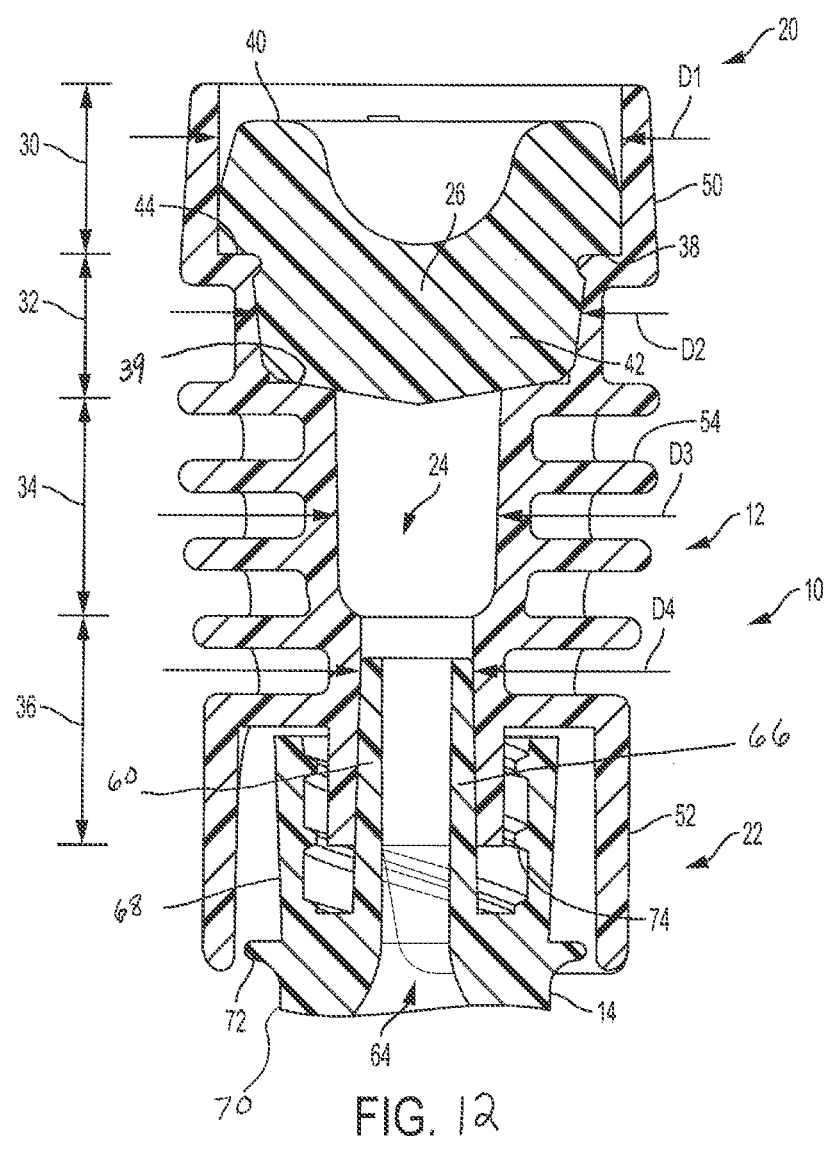
FIG. 12 is a cross-sectional view of a closure in accordance with an embodiment of the present invention.

Referring to FIG. 12, in one embodiment, the cap 12 defines a first cap channel portion 30 therein, a second cap channel portion 32 therein, a third cap channel portion 34 therein, and a fourth cap channel portion 36 therein. Referring to FIG. 12, the first cap channel portion 30 has a first diameter D1, the second cap channel portion 32 has a second diameter D2, the third cap channel portion 34 has a third diameter D3, and the fourth cap channel portion 36 has a fourth diameter D4. In one embodiment, the first diameter D1 is greater than the second diameter D2, the second diameter D2 is greater than the third diameter D3, and the third diameter D3 is greater than the fourth diameter D4. The first cap channel portion 30, the second cap channel portion 32, and the third cap channel portion 34 are configured to securely receive a stopper 26 within the cap 12. The fourth cap channel portion 36 is configured to securely receive a portion of the adapter 14.

In one embodiment, the cap 12 defines a first ledge portion 38 that is located between the first cap channel portion 30 and the second cap channel portion 32. Also, in one embodiment, the cap 12 defines a second ledge portion 39 that is located between the second cap channel portion 32 and the third cap channel portion 34.

Referring to FIG. 12, in one embodiment, the stopper 26 has a top portion 40, a bottom portion 42, and defines a shoulder portion 44 between the top portion 40 and the bottom portion 42.

The first cap channel portion 30, the second cap channel portion 32, and the third cap channel portion 34 are configured to securely receive a stopper 26 within the cap 12. For example, in one embodiment, the stopper 26 is contained within the cap channel 24 such that the top portion 40 of the stopper 26 is within the first cap channel portion 30 and the bottom portion 42 of the stopper 26 is within the second cap channel portion 32. In this manner, the stopper 26 is securely contained within the cap channel 24 such that the shoulder portion 44 of the stopper 26 contacts the first ledge portion 38 of the cap 12 and the bottom portion 42 of the stopper 26 contacts the second ledge portion 39 of the cap 12 to restrain the stopper 26 within the cap channel 24. Such engagement secures and restrains the stopper 26 within the cap channel 24 when the stopper 26 is punctured. For example, in one embodiment, when a non-patient needle 114 of a tube holder 112 contacts and pierces the stopper 26, the stopper 26 is prevented from significant relative movement relative to the cap 12.

In one embodiment, the cap 12 also includes a first wall shield portion 50, a second wall shield portion 52, radial ribs 54, longitudinal ribs 56, and outer surface 58. Referring to FIG. 12, the second cap end 22 includes a second wall shield portion 52.

Referring to FIG. 12, the first cap end 20 includes a first wall shield portion 50 that protectively shields the stopper 26. For example, the first wall shield portion 50 provides a physical barrier that extends beyond the top portion 40 of the stopper 26 as shown in FIG. 12. In this manner, the stopper 26 is safely contained within the cap 12 and the first wall shield portion 50 provides protection from a portion of a blood sample on the stopper 26 splashing externally from the cap 12.

Referring to FIGS. 9-12, an outer surface 58 of the cap 12 includes radial ribs 54 and longitudinal ribs 56. The ribs 54, 56 provide gripping surfaces that make it easy for a user's fingers to grip the cap 12 of the closure 10. For example, the ribs 54, 56 provide ergonomically shaped surfaces that aid the user in manipulating the closure 10 and using the closure 10 in a blood collection procedure, and may provide multiple finger grip positions for the user.

Figure 7A:
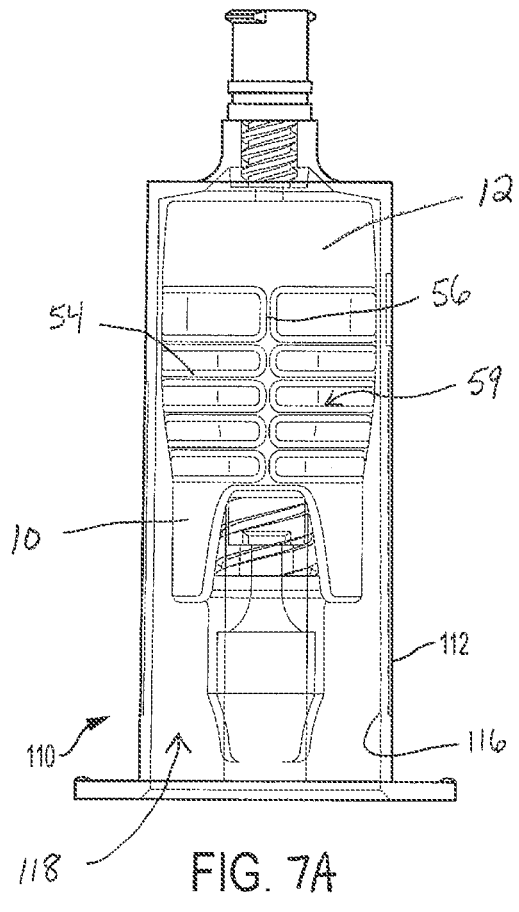
FIG. 7A is an elevation view of a closure of a biological fluid collection system connected to a first blood collection device in accordance with an embodiment of the present invention.
Figure 9:
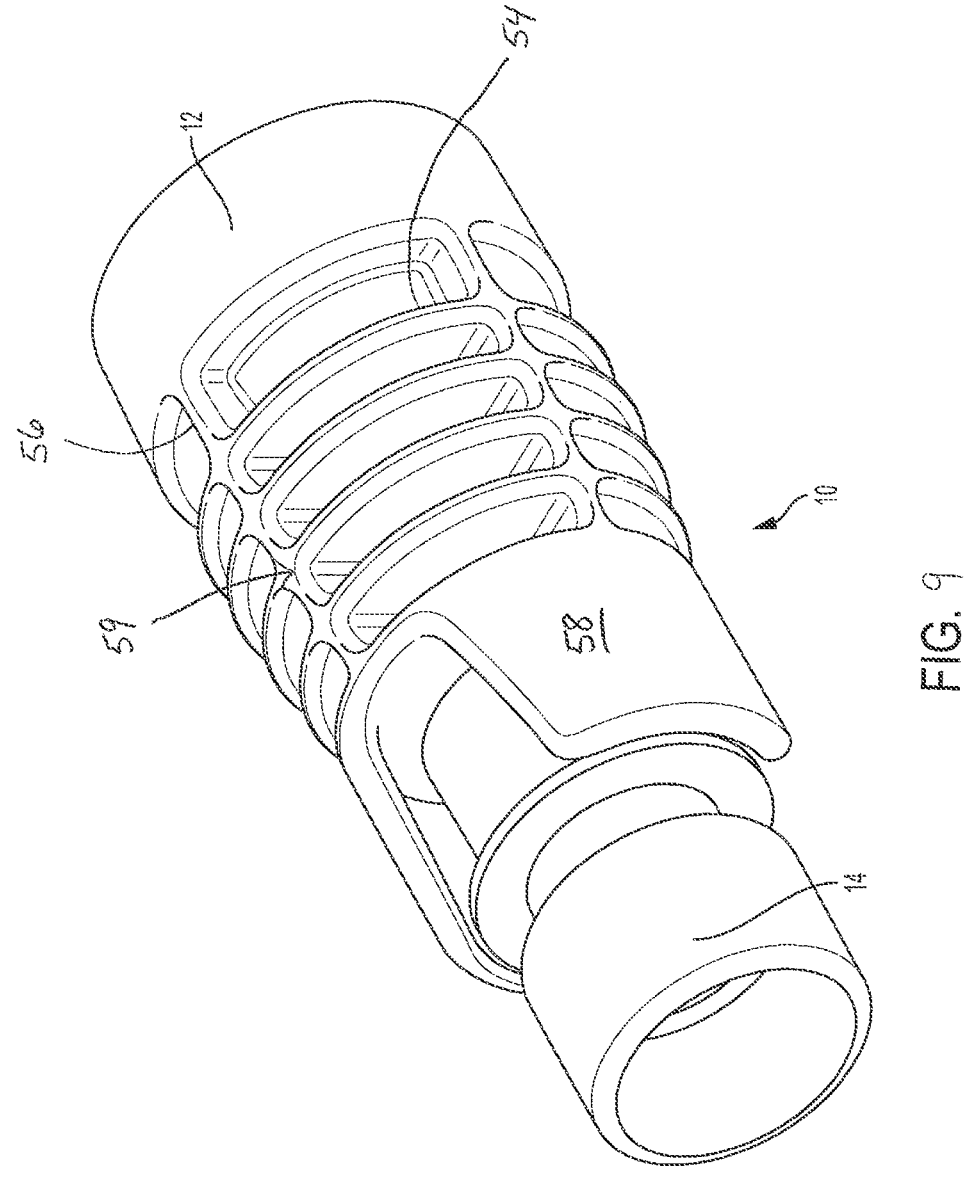
FIG. 9 is a perspective view of a closure in accordance with an embodiment of the present invention.

Referring to FIG. 7A, the ribs 54, 56 also provide touch point portions 59 that ensure that the closure 10 is properly aligned and positioned within a tube holder 112. For example, the touch point portions 59 extend outward so that the width of the cap 12 is slightly smaller than the inner diameter of the tube holder 112 and touch a portion of an interior surface 116 of the tube holder 112. This provides a centering and alignment mechanism when the closure 10 is inserted within a tube holder 112. In this manner, the cap 12 of the closure 10 is received within the tube holder 112 in a proper orientation, e.g., the cap 12 is properly centered within the tube holder 112 such that a non-patient needle 114 of the tube holder 112 is properly aligned with a stopper 26 of the closure 10.

Figure 11:
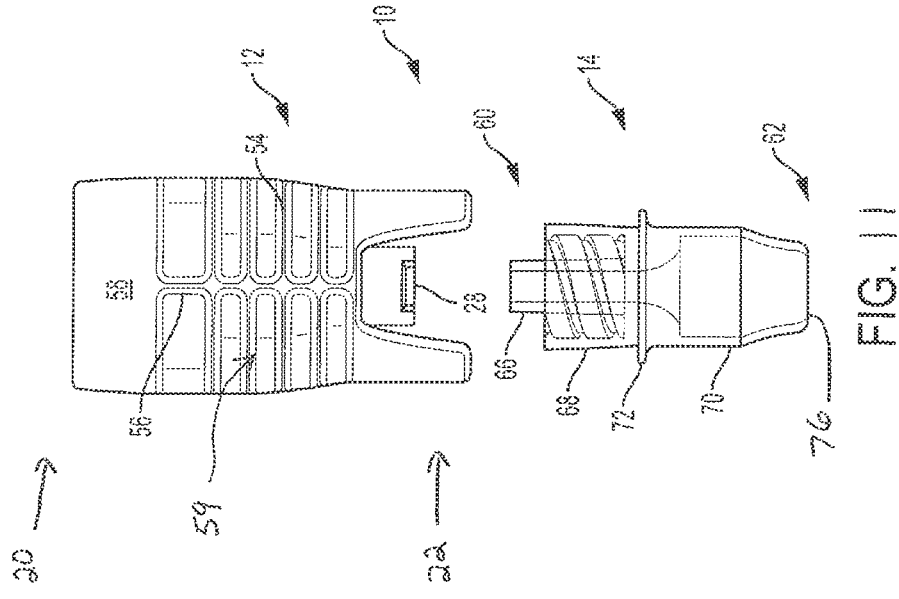
FIG. 11 is an exploded view of a closure in accordance with an embodiment of the present invention.
Figure 10:
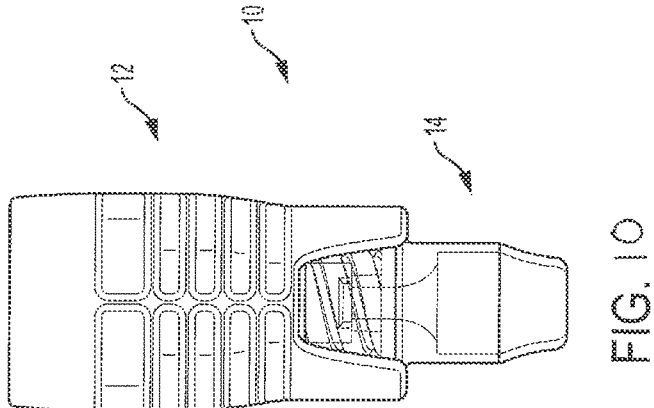
FIG. 10 is an elevation view of a closure in accordance with an embodiment of the present invention.

In one embodiment, the adapter or connector 14 includes a first adapter end 60, a second adapter end 62, and defines an adapter channel 64 therein. The adapter 14 has an adapter connection portion 66 at the first adapter end 60. Referring to FIG. 11, in one embodiment, the adapter 14 includes a first portion 68, a second portion 70, and a flange portion 72 between the first portion 68 and the second portion 70. In one embodiment, the adapter connection portion 66 comprises a second Luer connection portion for mating connection with the first Luer connection portion of the cap connection portion 28. In one embodiment, the closure 10 is removably connectable with the first mixer end 210 of the mixer 6. For example, the second adapter end 62 includes a connector 76 that is removably connectable with the first mixer connector 212 of the mixer 6.

Referring to FIGS. 9-12, in one embodiment, the adapter 14 is removably connectable to the cap 12. For example, the adapter connection portion 66 is removably connectable with the cap connection portion 28 of the cap 12. In one embodiment, the cap connection portion 28 comprises a first Luer connection portion and the adapter connection portion 66 comprises a second Luer connection portion for mating connection with the first Luer connection portion. In one embodiment, the connection portions 28, 66 form an ISO standard Luer interface. In one embodiment, the connection portions 28, 66 form a spin lock Luer interface. For example, the adapter connection portion 66 may include a Luer lock thread portion 74. In another embodiment, the connection portions 28, 66 form a slip lock Luer interface. The cap connection portion 28 and the adapter connection portion 66 may be threaded or snap-fit together to form a secure connection.

With the adapter 14 connected to the cap 12, the adapter 14 is locked to the cap 12, i.e., the adapter 14 and the cap 12 are protectively sealed theretogether. Referring to FIG. 12, with the adapter 14 connected to the cap 12, the cap channel 24 is in fluid communication with the adapter channel 64.

Referring to FIG. 12, with the cap 12 connected to the adapter 14, the second wall shield portion 52 of the cap 12 protectively shields the first adapter end 60 and the first portion 68 of the adapter 14. For example, the second wall shield portion 52 provides a physical barrier that extends beyond the flange portion 72 of the adapter 14 as shown in FIG. 12. In this manner, the second wall shield portion 52 and the flange portion 72 form a protective physical barrier that protectively shields the first adapter end 60 and the first portion 68 of the adapter 14.

Figures 2, 3, 4:
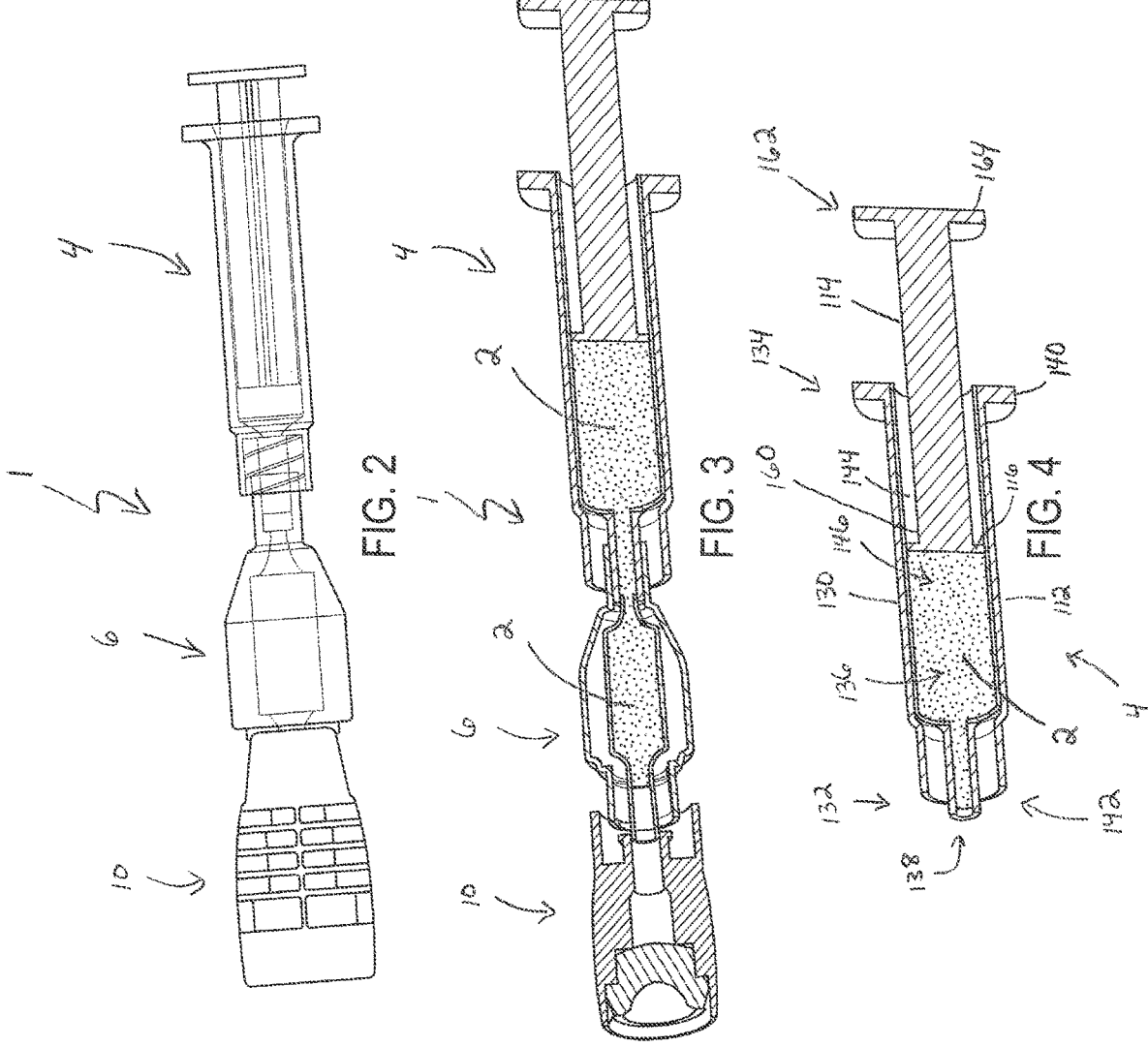
FIG. 2 is an assembled view of a biological fluid collection system in accordance with an embodiment of the present invention.
FIG. 3 is a cross-sectional view of the biological fluid collection system of FIG. 2 with a blood sample drawn within a syringe assembly in accordance with an embodiment of the present invention.
FIG. 4 is a cross-sectional view of the syringe assembly of FIG. 3 with a mixer and a closure removed from the syringe assembly in accordance with an embodiment of the present invention.

Referring to FIGS. 1-3, a closure 10 of the present disclosure is able to protectively seal a biological fluid collection system 1, e.g., a mixer 6 and a syringe assembly 4. For example, in one embodiment, the closure 10 is removably connectable to a first mixer end 210 of mixer 6. With the closure 10 connected to the mixer 6, the closure 10 seals the biological fluid collection system 1.

Referring to FIG. 2, the closure 10 can be engaged with and protectively seal biological fluid collection system 1 to seal the mixer 6. The closure 10 allows for the safe introduction of a blood sample into the mixer 6 and the syringe assembly 4.

The closure 10 of the present disclosure allows for connection to multiple different blood collection devices. For example, in one embodiment, the closure 10 allows for connection to a first blood collection device 110 (FIG. 7) in a first configuration and connection to a second blood collection device 120 (FIG. 8) in a second configuration. An advantage of the closure 10 of the present disclosure is that it enables a single closure device to accommodate a variety of connection options.

Referring to FIGS. 7, in a first configuration, with the cap 12 connected to the adapter 14, the closure 10 may be connected to a first blood collection device 110 via the cap 12. In some embodiments, the cap 12 can be directly connected to a first blood collection device 110 without the adapter 14. In one embodiment, the first blood collection device 110 includes a tube holder 112 having a non-patient needle 114 through which biological fluid is passed, and an interior wall or surface 116 which defines a tube cavity 118.

In a second configuration, with the cap 12 disconnected from the adapter 14, the closure 10 may be connected to a second blood collection device 120 via the adapter 14. Referring to FIG. 8, in some embodiments, the closure 10 can be removed and the first mixer end 210 of the mixer 6 can be connected to a second blood collection device 120. In one embodiment, the second blood collection device 120 includes a line 122 ending in a Luer connector 124.

Referring to FIGS. 1-6, the biological fluid collection system 1 includes a syringe assembly 4 for automatic drawing of a stabilized blood sample 2 within the syringe assembly 4. In one embodiment, the syringe assembly 4 includes a collection chamber 136 and the syringe assembly 4 is able to create a vacuum that draws a sample 2 through a mixer 6 and into the collection chamber 136. The syringe 4 allows for easy drawing of a sample and dispensing of a stabilized sample.

Referring to FIGS. 1-6, in one embodiment, the syringe assembly 4 includes a syringe barrel 112, a plunger 114, and a stopper 116. Referring to FIGS. 1-6, the syringe barrel 112 generally includes a barrel body or sidewall 130 extending between a first or distal end 132 and a second or proximal end 134. The sidewall 130 defines a collection chamber, elongate aperture, or interior chamber 136 of the syringe barrel 112. In one embodiment, an interior chamber 136 may span the extent of the syringe barrel 112 so that the syringe barrel 112 is cannulated along its entire length. In one embodiment, the syringe barrel 112 may be in the general form of an elongated cylindrical barrel as is known in the art in the general shape of a hypodermic syringe. In alternative embodiments, the syringe barrel 112 may be in other forms for containing a fluid for delivery, such as in the general form of an elongated rectangular barrel, for example. The syringe barrel 112 may be formed of glass, or may be injection molded from thermoplastic material such as polypropylene and polyethylene according to techniques known to those of ordinary skill in the art, though it is to be appreciated that the syringe barrel 112 may be made from other suitable materials and according to other applicable techniques. In certain configurations, the syringe barrel 112 may include an outwardly extending flange 140 about at least a portion of the proximal end 134. The flange 140 may be configured for easy grasping by a medical practitioner.

The first end 132 of the syringe barrel 112 includes an outlet opening 138 which is in fluid communication with the chamber 136. In one embodiment, the barrel 112 of the syringe assembly 4 is removably connectable with a second mixer end 214 of the mixer 6. For example, the first end 132 of the syringe barrel 112 includes a connector 142 that is removably connectable with the second mixer connector 216 of the mixer 6.

The proximal end 134 of the syringe barrel 112 is generally open-ended, but is intended to be closed off to the external environment as discussed herein. The syringe barrel 112 may also include markings, such as graduations located on the sidewall 130, for providing an indication as to the level or amount of fluid contained within the interior chamber 136 of the syringe barrel 112. Such markings may be provided on an external surface of the sidewall 130, an internal surface of the sidewall 130, or integrally formed or otherwise within the sidewall 130 of the syringe barrel 112. In other embodiments, alternatively, or in addition thereto, the markings may also provide a description of the contents of the syringe or other identifying information as may be known in the art, such as maximum and/or minimum fill lines.

Referring to FIGS. 1-6, the syringe assembly 4 includes a stopper 116 which is moveably or slidably disposed within the interior chamber 136, and in sealing contact with the internal surface of the sidewall 130 of the syringe barrel 112, thereby separating the interior chamber 136 into a proximal chamber 144 adjacent a proximal end 134, and a distal chamber 146 adjacent a distal end 132. The stopper 116 is sized relative to the syringe barrel 112 to provide sealing engagement with the interior surface of sidewall 130 of the syringe barrel 112. Additionally, in one embodiment, the stopper 116 may include one or more annular ribs extending around the periphery of the stopper 116 to increase the sealing engagement between the stopper 116 and the interior surface of the sidewall 130 of the syringe barrel 112. In alternate embodiments, a singular O-ring or a plurality of O-rings may be circumferentially disposed about the stopper 116 to increase the sealing engagement with the interior surface of the sidewall 130.

The stopper 116 is slidably disposed within the chamber 136 of the barrel 112. The stopper 116 is transitionable between a first stopper position (FIG. 2), in which the stopper 116 is a first distance from the first end 132 of the barrel 112, and a second stopper position (FIG. 3), in which the stopper 116 is a second distance from the first end 132 of the barrel 112, the second distance being greater than the first distance.

Referring to FIGS. 1-6, the syringe assembly 4 further includes a plunger 114 which provides a mechanism for retracting and advancing a stopper 16. The plunger 114 includes a first plunger end 160, a second plunger end 162, and a flange 164. In one embodiment, a portion of the first plunger end 160 is engaged with the stopper 116, wherein movement of the plunger 114 away from the first end 132 of the barrel 112 moves the stopper 116 to the second stopper position (FIG. 3), thereby creating a vacuum that draws the sample 2 through the mixer 6 and into the collection chamber 136 of the syringe assembly 4.

Referring to FIGS. 2 and 3, in one embodiment, the use of a syringe assembly 4 to fill a chamber 136 of a syringe barrel 112 with a stabilized blood sample 2 will now be described. With the syringe assembly 4 in a position in which a stopper 116 is located adjacent a distal end 132 of the syringe barrel 112 (FIG. 2), when it is desired to aspirate or pull the blood sample 2 through the mixer 6 and into the chamber 136 of the syringe barrel 112, a user moves a flange 164 of a plunger 114 in a direction away from the proximal end 134 of the syringe barrel 112 until the desired amount of stabilized blood sample 2 is pulled into the chamber 136 of the syringe barrel 112. In this manner, movement of the stopper 116 and the plunger 114 in this direction creates a vacuum inside the distal chamber 146 of the syringe barrel 112.

The biological fluid collection system 1 includes a mixer 6 that allows for automatic and passive mixing of a blood sample 2 with a sample stabilizer 8, such as an anticoagulant, blood stabilizer, or another additive, as the blood sample 2 flows through the closure 10 to the collection chamber 136 of the syringe assembly 4. In one embodiment, the mixer 6 includes a first mixer end 210 having a first mixer connector 212, a second mixer end 214 having a second mixer connector 216, and a mixer structure 218.

In one embodiment, the first mixer end 210 is removably connectable to the closure 10 and the second mixer end 214 is removably connectable to the syringe assembly 4. The closure 10 is removably connectable with the first mixer end 210 of the mixer 6, e.g., the second adapter end 62 includes a connector 76 that is removably connectable with the first mixer connector 212 of the mixer 6. The barrel 112 of the syringe assembly 4 is removably connectable with a second mixer end 214 of the mixer 6, e.g., the first end 132 of the syringe barrel 112 includes a connector 142 that is removably connectable with the second mixer connector 216 of the mixer 6. In some embodiments, the mixer 6 is removably connectable to the closure 10 and the syringe assembly 4 via a press fit.

The mixer structure 218 of the mixer 6 is able to effectuate distributed mixing of a sample stabilizer 8 within a blood sample 2. The mixer structure 218 may have any suitable structure or form as long as it provides for the mixing of the blood sample 2 with a sample stabilizer 8, such as an anticoagulant or other additive, as the blood sample 2 passes through the mixer 6 and into the collection chamber 136 of the syringe assembly 4.

Figure 13:
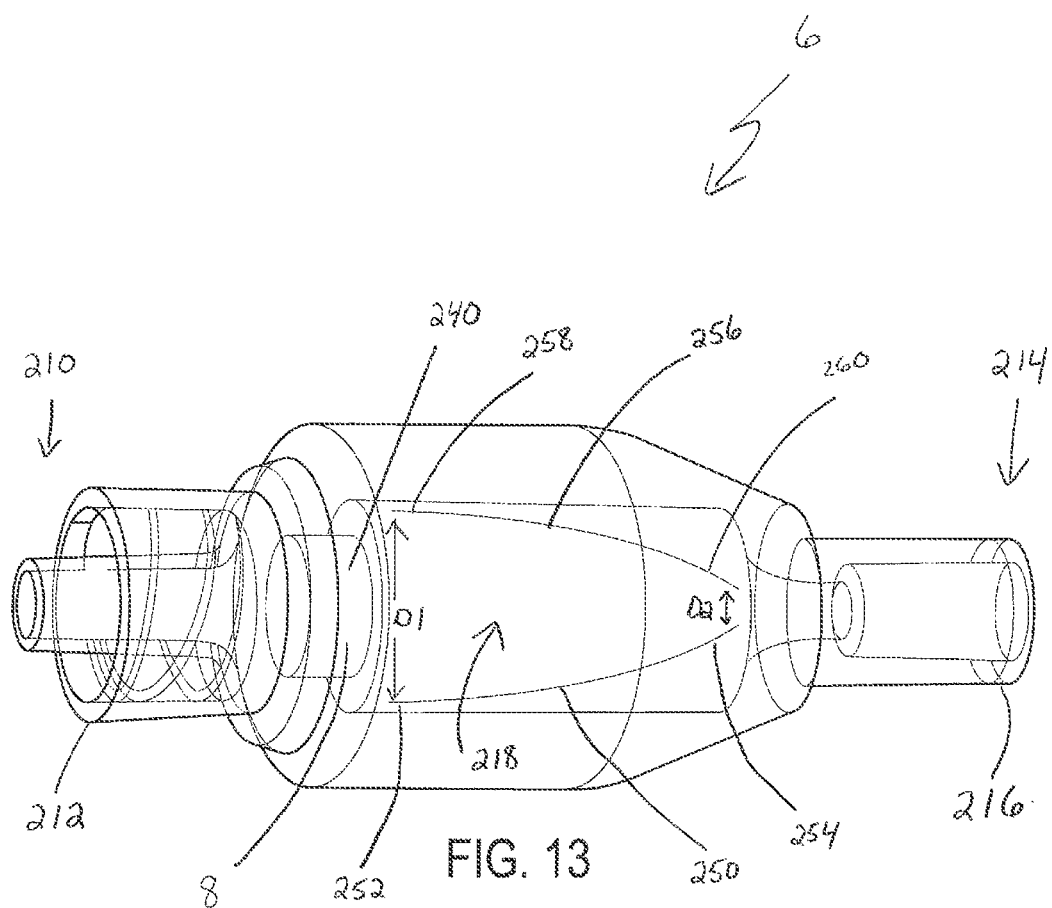
FIG. 13 is a perspective view of a mixer in accordance with an embodiment of the present invention.

Referring to FIG. 13, in one embodiment, the mixer structure 218 includes a first curved wall 250 having a first inlet end 252 and a first exit end 254, and a second curved wall 256 having a second inlet end 258 and a second exit end 260. The first inlet end 252 is spaced a first distance D1 from the second inlet end 258 and the first exit end 254 is spaced a second distance D2 from the second exit end 260. In one embodiment, the second distance D2 is less than the first distance D1.

The mixer structure 218 receives the sample 2 and the sample stabilizer 8 therein and effectuates distributed mixing of the sample stabilizer 8 within the sample 2. The mixer structure 218 effectuates distributed mixing of the sample stabilizer 8 within the sample 2 and prevents a very high sample stabilizer concentration in any portion of the blood sample 2. This prevents underdosing of the sample stabilizer 8 in any portion of the blood sample 2. The mixer structure 218 effectuates distributed mixing of the sample stabilizer 8 within the sample 2 so that an approximately equal amount and/or concentration of the sample stabilizer 8 is dissolved throughout the blood sample 2, e.g., an approximately equal amount and/or concentration of the sample stabilizer 8 is dissolved into the blood sample 2 from a front portion of the blood sample 2 to a rear portion of the blood sample 2.

The mixer 6 and the collection chamber 136 of the syringe assembly 4 are connected and provided in fluid communication via the second mixer end 214 and the outlet opening 138. The mixer 6 and the collection chamber 136 of the syringe assembly 4 are positioned such that a biological fluid sample, such as a blood sample 2, collected into the collection chamber 136 of the syringe assembly 4 via the closure 10 and the mixer 6, will first pass through a sample stabilizer 8 within the mixer 6, then the blood sample 2 and the sample stabilizer 8 pass through the mixer structure 218, and subsequently the sample 2 with the sample stabilizer 8 properly mixed therein flows out the second mixer end 214 into the collection chamber 136 of the syringe assembly 4. In this way, the blood sample 2 may be mixed with a sample stabilizer 8, such as an anticoagulant or other additive, provided within the mixer 6, before passing through the mixing structure 218 for proper mixing of the sample stabilizer 8 within the blood sample 2, and then the stabilized sample is received and stored within the collection chamber 136 of the syringe assembly 4.

In one embodiment, a sample stabilizer 8 is disposed between the first mixer end 210 and the mixing structure 218. The mixer 6 of the present disclosure provides passive and fast mixing of a blood sample 2 with the sample stabilizer 8. For example, the mixer 6 allows for passive mixing of the blood sample 2 with an anticoagulant or another additive, such as a blood stabilizer, as the blood sample 2 flows through the mixing structure 218.

The sample stabilizer 8 can be an anticoagulant, or a substance designed to preserve a specific element within the blood such as, for example, RNA, protein analyte, or other element. In one embodiment, the sample stabilizer 8 is disposed between the first mixer end 210 and the mixing structure 218. In other embodiments, the sample stabilizer 8 may be disposed in other areas within the mixer 6.

Figures 14, 15:
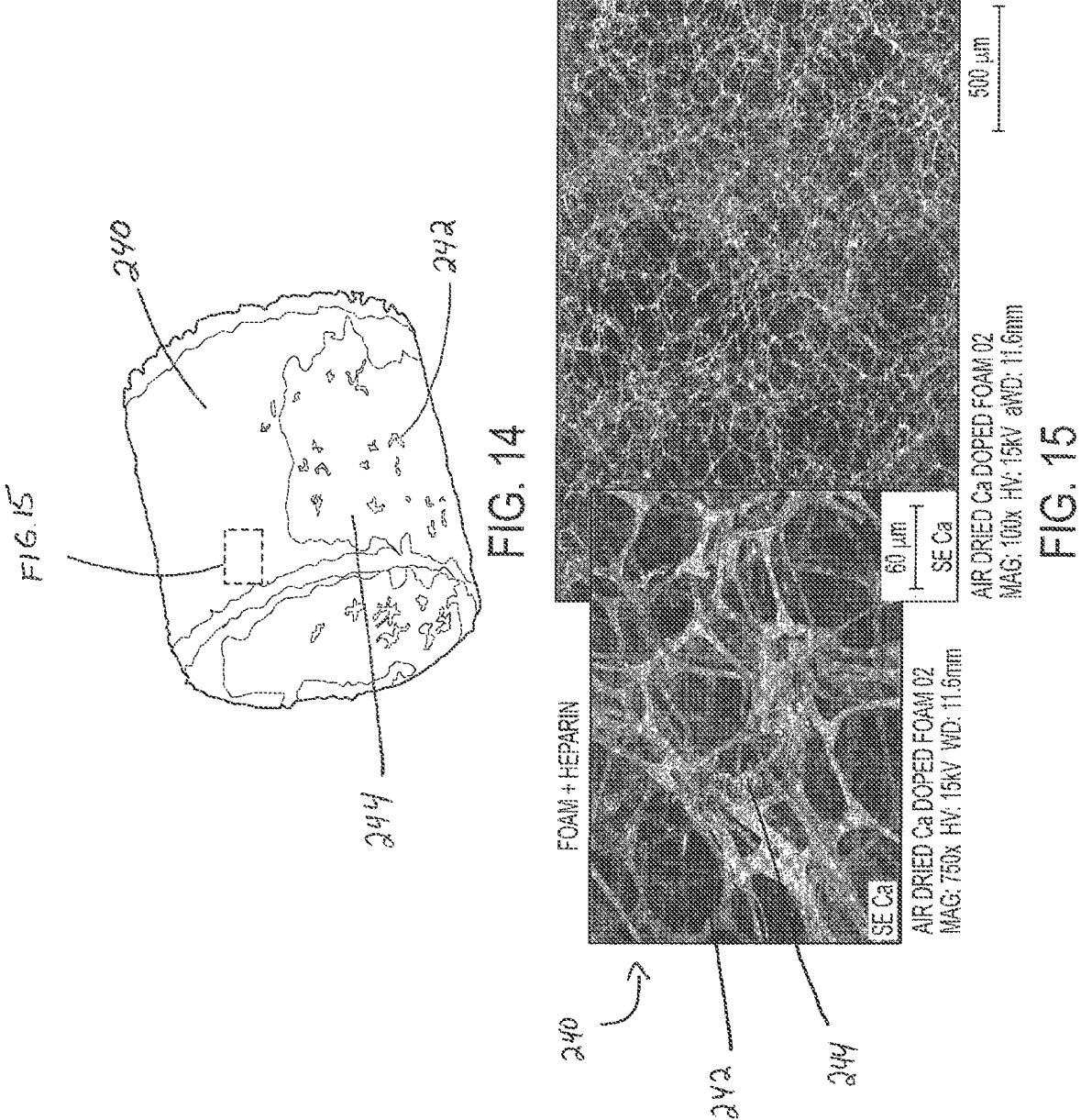
FIG. 14 is a perspective view of an open cell foam material in accordance with an embodiment of the present invention.
FIG. 15 is a microscopic view of the microstructure of an open cell foam material having a dry anticoagulant powder distributed throughout its microstructure in accordance with an embodiment of the present invention.

Referring to FIGS. 13-15, in one embodiment, the mixer 6 includes a material 240 including pores 242 that is disposed between the first mixer end 210 and the mixing structure 218 and a dry anticoagulant powder 244 that is within the pores 242 of the material 240. In this manner, the mixer 6 may include a dry anticoagulant, such as Heparin or EDTA, deposited on or within a portion of the mixer 6. In one embodiment, the material 240 is an open cell foam that contains dry anticoagulant dispersed within the cells of the open cell foam to promote the effectiveness of the flow-through mixing and anticoagulant uptake. In one embodiment, the sample stabilizer 8 is the dry anticoagulant powder 244.

In one embodiment, the open cell foam may be treated with an anticoagulant to form a dry anticoagulant powder finely distributed throughout the pores of the open cell foam. As the blood sample 2 enters the mixer 6, the blood sample 2 passes through the open cell foam and is exposed to the anticoagulant powder available throughout the internal pore structure of the open cell foam. In this manner, the sample 2 dissolves and mixes with the dry anticoagulant powder 244 while passing through the material 240 or open cell foam.

The open cell foam 240 may be a soft deformable open cell foam that is inert to blood, for example, a melamine foam, such as Basotect® foam commercially available from BASF, or may consist of a formaldehyde-melamine-sodium bisulfite copolymer. The open cell foam 240 may also be a flexible, hydrophilic open cell foam that is substantially resistant to heat and organic solvents. In one embodiment, the foam 240 may include a sponge material.

The anticoagulant or other additive may be introduced into the open cell foam 240 by soaking the foam in a liquid solution of the additive and water and subsequently evaporating the water forming a dry additive powder finely distributed throughout the internal structure of the foam 240.

Referring to FIGS. 3-6, after the biological fluid collection system 1 using mixer 6 to stabilize a blood sample 2 and collect the stabilized sample 2 in the collection chamber 136 of the syringe assembly 4, the closure 10 and the mixer 6 can be removed, and a stabilized sample 2 is left in the syringe assembly 4. A user may then use the syringe assembly 4 to dispense or transfer a stabilized blood sample 2 to a device intended to analyze the sample 2, e.g., such as a point-of-care testing device 320 (FIGS. 5 and 6), a cartridge tester, or a near patient testing device, while minimizing the exposure of the medical practitioner to the blood sample 2. In some embodiments, the stabilized blood sample 2 may be transferred into a point-of-care cartridge or point-of-care benchtop analyzer. A user may also send the stabilized sample 2 to the core lab for analysis.

Figure 5:
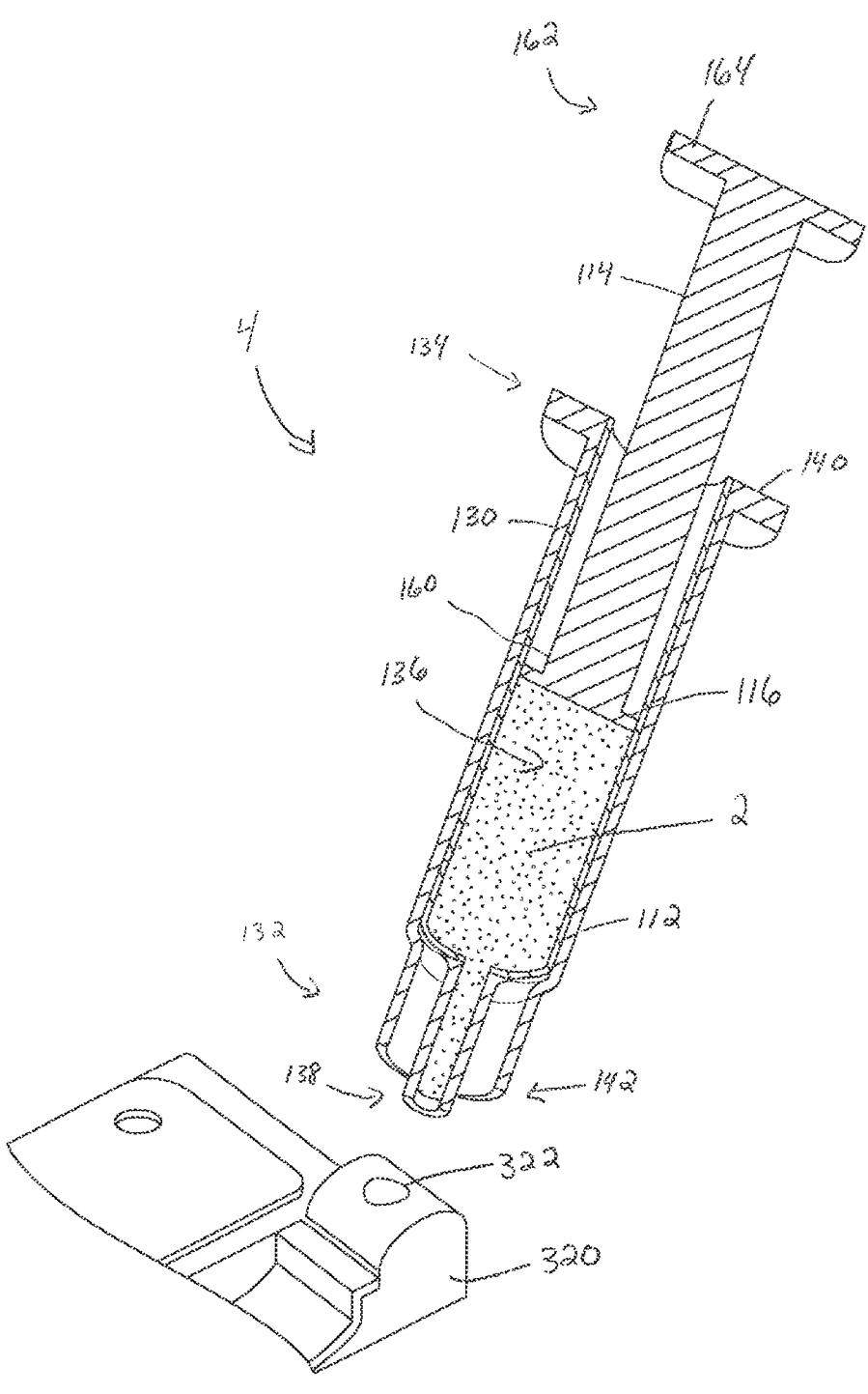
FIG. 5 is a cross-sectional perspective view of a syringe assembly in a first position with a blood sample contained therein adjacent a point-of-care testing device in accordance with an embodiment of the present invention.
Figure 6:
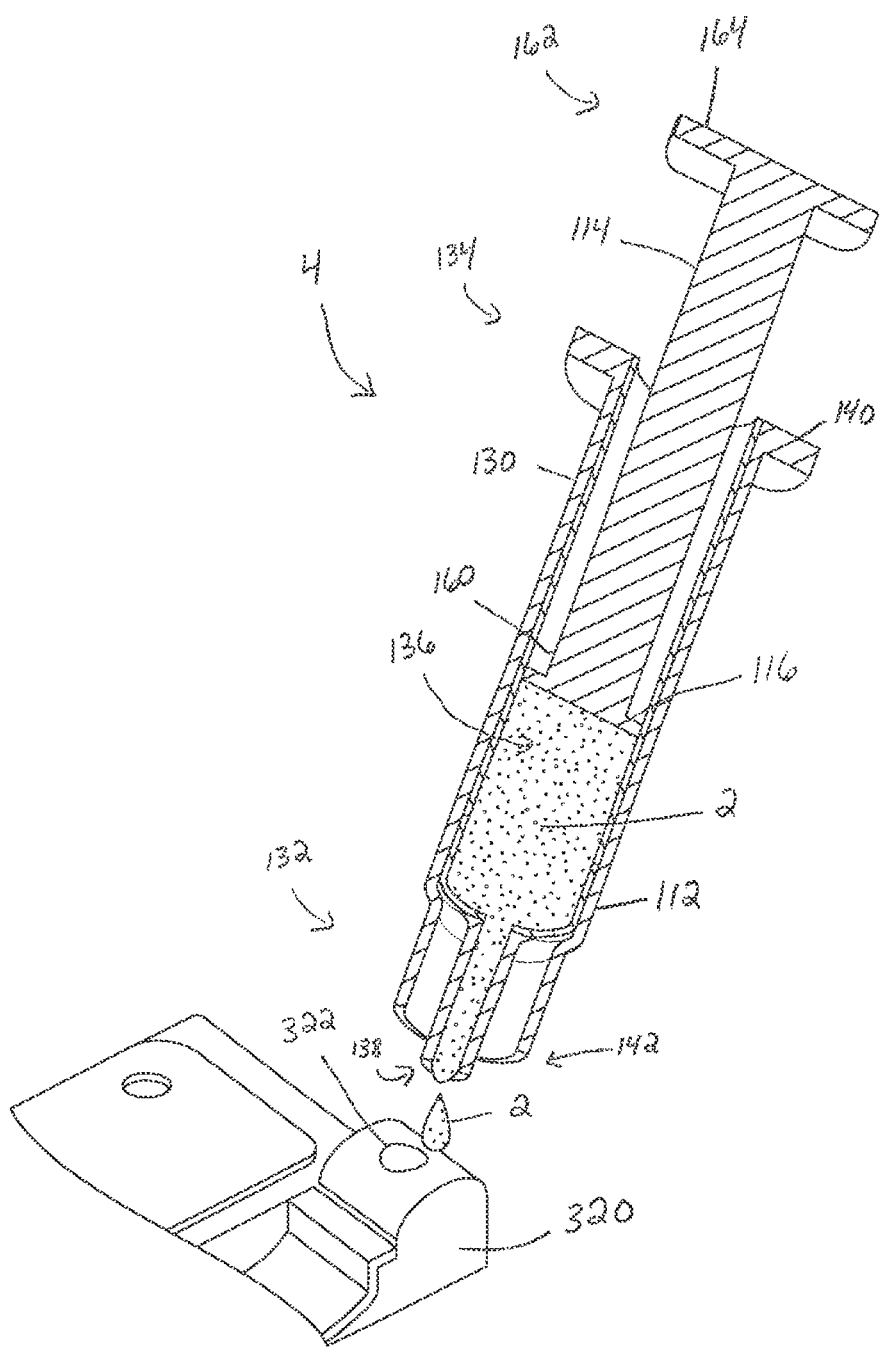
FIG. 6 is a cross-sectional perspective view of a syringe assembly in a second position with a blood sample contained therein adjacent a point-of-care testing device and dispensing a portion of a sample to the testing device in accordance with an embodiment of the present invention.

Referring to FIGS. 5 and 6, when it is desired to expel a stabilized blood sample 2 contained within a syringe barrel 112, a syringe assembly 4 is grasped with the user's thumb on a flange 164 of a plunger 114 and with the user's fingers grasping and extending around a flange 140 of the syringe barrel 112. In this manner, the syringe assembly 4 is grasped by a user in a well-known and well recognized manner similar to the operation of a conventional syringe. Next, the user effects a squeezing movement between the thumb on the flange 164 of the plunger 114 and four fingers grasping the flange 140 of the syringe barrel 112, thereby causing the flange 164 of the plunger 114 to move in a direction toward a proximal end 134 of the syringe barrel 112. In this manner, movement of a stopper 116 in this direction forces a desired amount of the stabilized blood sample 2 contained within a distal chamber 146 of the syringe barrel 112 to be forced out an outlet opening 138, i.e., movement of the stopper 116 towards a distal end 132 of the syringe barrel 112 reduces the volume of the distal chamber 146 and forces the stabilized blood sample 2 from the syringe barrel 112.

Referring to FIGS. 5 and 6, in one embodiment, a testing device 320 includes a receiving port 322 that is adapted to receive a portion of the syringe assembly 4 for closed transfer of at least a portion of the sample 2 from the syringe assembly 4 to the testing device 320.

The closure 10 of the present disclosure allows for connection to multiple different blood collection devices. For example, in one embodiment, the closure 10 allows for connection to a first blood collection device 110 (FIG. 7) in a first configuration and connection to a second blood collection device 120 (FIG. 8) in a second configuration. An advantage of the closure 10 of the present disclosure is that it enables a single closure device to accommodate a variety of connection options.

Referring to FIGS. 7, in a first configuration, with the cap 12 connected to the adapter 14, the closure 10 may be connected to a first blood collection device 110 via the cap 12. In some embodiments, the cap 12 can be directly connected to a first blood collection device 110 without the adapter 14. In one embodiment, the first blood collection device 110 includes a tube holder 112 having a non-patient needle 114 through which biological fluid is passed, and an interior wall or surface 116 which defines a tube cavity 118.

In a second configuration, with the cap 12 disconnected from the adapter 14, the closure 10 may be connected to a second blood collection device 120 via the adapter 14. Referring to FIG. 8, in some embodiments, the closure 10 can be removed and the first mixer end 210 of the mixer 6 can be connected to a second blood collection device 120. In one embodiment, the second blood collection device 120 includes a line 122 ending in a Luer connector 124.

The biological fluid collection system 1 of the present disclosure utilizes a mixer 6 and a closure 10 with a syringe 4. The syringe 4 and closure 10 allow a user to draw a sample 2 from either a Luer line or through a tube holder, or other blood collection device. The syringe 4 also allows for easy draw of a sample and dispensing of a stabilized sample.

The use of a mixer 6 enables automatic mixing of a sample stabilizer 8, such as an anticoagulant, and a blood sample 2 before collection within the syringe 4. The syringe 4 also provides a vacuum to draw in a blood sample 2 and functions as a dispensing mechanism for transfer of a stabilized blood sample to testing devices, cartridges, or benchtop instruments.

While this disclosure has been described as having exemplary designs, the present disclosure can be further modified within the spirit and scope of this disclosure. This application is therefore intended to cover any variations, uses, or adaptations of the disclosure using its general principles. Further, this application is intended to cover such departures from the present disclosure as come within known or customary practice in the art to which this disclosure pertains and which fall within the limits of the appended claims.

What is claimed is:

1. A biological fluid collection system adapted to receive a sample, the biological fluid collection system comprising:
   a mixer having a first mixer end and a second mixer end;
   a sample stabilizer disposed within the mixer; and
   a syringe assembly having a collection chamber, the syringe assembly removably connectable with the second mixer end, the syringe assembly creates a vacuum that draws the sample through the mixer and into the collection chamber; and
   a closure comprising a cap and an adapter, wherein the cap is removably connectable with the adapter and the adapter is removably connectable with the first mixer end of the mixer,
   wherein:
   with the cap connected to the adapter, the closure is connectable to a first blood collection device via the cap, and
   with the cap disconnected from the adapter, the closure is connectable to a second blood collection device via the adapter.

2. The biological fluid collection system of claim 1, wherein:
   the cap has a first cap end, a second cap end, and defines a cap channel therein, the cap having a pierceable self-sealing stopper within a portion of the cap channel and a cap connection portion at the second cap end; and
   the adapter has a first adapter end, a second adapter end, and defines an adapter channel therein, the adapter having an adapter connection portion at the first adapter end, the cap connection portion removably connectable with the adapter connection portion.

3. The biological fluid collection system of claim 1, wherein the first blood collection device is a tube holder.

4. The biological fluid collection system of claim 1, wherein the second blood collection device is a line ending in a Luer connector.

5. The biological fluid collection system of claim 1, wherein the syringe assembly comprises:
   a barrel defining the collection chamber and having a first end, a second end, and a sidewall therebetween;
   a stopper slidably disposed within the collection chamber of the barrel, the stopper sized relative to the collection chamber to provide sealing engagement with the sidewall of the barrel, the stopper transitionable between a first stopper position, in which the stopper is a first distance from the first end of the barrel, and a second stopper position, in which the stopper is a second distance from the first end of the barrel, the second distance greater than the first distance; and a plunger having a first plunger end and a second plunger end, a portion of the first plunger end engaged with the stopper, wherein movement of the plunger away from the first end of the barrel moves the stopper to the second stopper position thereby creating the vacuum that draws the sample through the mixer and into the collection chamber.

6. The biological fluid collection system of claim 5, wherein, with the syringe assembly connected to the mixer, the barrel is in fluid communication with the mixer.

7. The biological fluid collection system of claim 1, wherein the mixer effectuates distributed mixing of the sample stabilizer within the sample.

8. The biological fluid collection system of claim 1, wherein the mixer comprises:
   a material including pores; and
   a dry anticoagulant powder within the pores of the material.

9. The biological fluid collection system of claim 8, wherein the sample is configured to dissolve and mix with the dry anticoagulant powder while passing through the material.

10. The biological fluid collection system of claim 8, wherein the material is an open cell foam.

11. The biological fluid collection system of claim 8, wherein the sample stabilizer is the dry anticoagulant powder.

12. The biological fluid collection system of claim 1, wherein the sample is a blood sample.

13. A biological fluid collection and testing system adapted to receive a sample, the biological fluid collection and testing system comprising:
   a biological fluid collection device, comprising:
      a mixer having a first mixer end and a second mixer end;
      a sample stabilizer disposed within the mixer;
      a syringe assembly having a collection chamber, the syringe assembly removably connectable with the second mixer end, the syringe assembly creates a vacuum that draws the sample through the mixer and into the collection chamber; and
      a closure comprising a cap and an adapter, wherein the cap is removably connectable with the adapter and the adapter is removably connectable with the first mixer end of the mixer,
      wherein:
      with the cap connected to the adapter, the closure is connectable to a first blood collection device via the cap, and
      with the cap disconnected from the adapter, the closure is connectable to a second blood collection device via the adapter; and
   a testing device having a receiving port adapted to receive a portion of the syringe assembly for closed transfer of at least a portion of the sample from the syringe assembly to the testing device.

14. The biological fluid collection and testing system of claim 13, wherein:
   the cap has a first cap end, a second cap end, and defines a cap channel therein, the cap having a pierceable self-sealing stopper within a portion of the cap channel and a cap connection portion at the second cap end; and
   the adapter has a first adapter end, a second adapter end, and defines an adapter channel therein, the adapter having an adapter connection portion at the first adapter end, the cap connection portion removably connectable with the adapter connection portion.

15. The biological fluid collection and testing system of claim 13, wherein the first blood collection device is a tube holder.

16. The biological fluid collection and testing system of claim 13, wherein the second blood collection device is a line ending in a Luer.

17. The biological fluid collection and testing system of claim 13, wherein the syringe assembly comprises:

a barrel defining the collection chamber and having a first end, a second end, and a sidewall therebetween;

a stopper slidably disposed within the collection chamber of the barrel, the stopper sized relative to the collection chamber to provide sealing engagement with the sidewall of the barrel, the stopper transitionable between a first stopper position, in which the stopper is a first distance from the first end of the barrel, and a second stopper position, in which the stopper is a second distance from the first end of the barrel, the second distance greater than the first distance; and a plunger having a first plunger end and a second plunger end, a portion of the first plunger end engaged with the stopper, wherein movement of the plunger away from the first end of the barrel moves the stopper to the second stopper position thereby creating the vacuum that draws the sample through the mixer and into the collection chamber.

\* \* \* \* \*